United States Patent [19]
Michne et al.

[11] Patent Number: 6,057,332
[45] Date of Patent: May 2, 2000

[54] SUBSTITUTED 1,4-DIHYDROPYRIMIDINE-5-CARBOXYLATE COMPOUNDS, THEIR PREPARATION AND USES

[75] Inventors: William F. Michne; M. Edward Pierson, Jr., both of Pittsford, N.Y.

[73] Assignee: Astra Aktiebolag, Sodertalje, Sweden

[21] Appl. No.: 09/171,172

[22] PCT Filed: Jun. 22, 1998

[86] PCT No.: PCT/SE98/01207

§ 371 Date: Oct. 14, 1998

§ 102(e) Date: Oct. 14, 1998

[87] PCT Pub. No.: WO99/01437

PCT Pub. Date: Jan. 14, 1999

[30] Foreign Application Priority Data

Jul. 2, 1997 [SE] Sweden ................................. 9702563

[51] Int. Cl.[7] ..................... A01N 43/54; A61K 31/505; C07D 239/02
[52] U.S. Cl. ..................... 514/272; 514/274; 544/297; 544/316
[58] Field of Search ..................... 544/297, 317; 514/272, 274

[56] References Cited

FOREIGN PATENT DOCUMENTS 0 202 654 A2  11/1986  European Pat. Off. .
0 697 407 A1  2/1996   European Pat. Off. .

OTHER PUBLICATIONS

Varadi et al, "Molecular determinants of $Ca^{2+}$ channel . . . ," TiPS, vol. 16, pp. 43–49 (1995).

Triggle et al, "Synthetic Organic Ligands Active at . . . ," Ann. New York Acad. Sci., vol. 635, pp. 123–138 (1991).

Bowersox et al, "Neuronal Voltage–Sensitive Calcium Channels," DN&P, vol. 7, No. 5, pp. 261–268 (1994).

Pat. Abs. of Japan, vol. 12, No. 155 (C–494) 3002 (1988).

Cho et al, "Dihydropyrimidines: Novel Calcium . . . ," J. Med. Chem., vol. 32, pp. 2399–2406 (1989).

*Primary Examiner*—Mukund J. Shah
*Assistant Examiner*—Tamthon N. Truong
*Attorney, Agent, or Firm*—Nixon & Vanderhye

[57] ABSTRACT

There are provided novel compounds of formula (I)

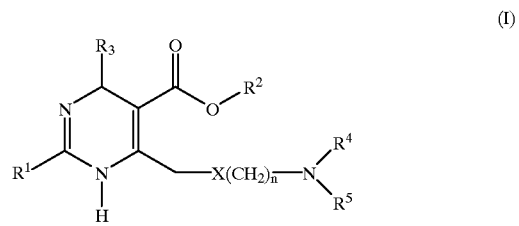

including their 3,4-dihydropyrimidine tautomer form, wherein $R^1$, $R^2$, $R^3$, $R^4$, $R^5$, X and n are as defined in the specification, and optical isomers and racemates thereof and pharmaceutically acceptable salts thereof; together with processes for their preparation, compositions containing them and their use in therapy. The compounds are antagonists of N-type neuronal calcium channels useful in the treatment of cerebrovascular ischaemia and pain.

20 Claims, No Drawings

SUBSTITUTED 1,4-DIHYDROPYRIMIDINE-5-CARBOXYLATE COMPOUNDS, THEIR PREPARATION AND USES

This application is a 371 application of PCT/SE98/01207, filed Jun. 22, 1998.

FIELD OF INVENTION

This invention relates to novel 2-alkylheterodihydropyrimidine derivatives, processes for their preparation, pharmaceutical compositions containing them and their use in therapy. A further objective is to provide compounds which are potent ligands for N-type neuronal calcium channels.

BACKGROUND OF THE INVENTION

It is well known that there are several different types of voltage-gated calcium channels which can be distinguished on the basis of biophysical and pharmacological properties. These calcium channels are defined by differences in the amino acid sequence of the $\alpha_1$ subunits ("Molecular Determinants of $Ca^{2+}$ Channel Function and Drug Action" TiPS 1995, 16, 43–49), and by different sensitivities to various ligands ("Synthetic Organic Ligands Active at Voltage-Gated Calcium Channels", *Ann. N.Y. Acad. Sci.*, 1991, 635, 123–138). These publications teach that the L-type calcium channel differs from the N-type calcium channel in regard to the amino acid sequence of the $\alpha_1$ subunits and the sensitivity to dihydropyridines (L-channels are sensitive, N-channels are not) and the sensitivity to ω-Conotoxins GVIA and MVIIA (N-channels are sensitive, L-channels are not).

L-Type calcium channel antagonists are clinically proven compounds for the treatment of cardiovascular disease, particularly hypertension.

The use of compounds which bind to N-type neuronal calcium channels has been discussed with respect to the treatment of a range of disorders involving abnormal calcium flux in cells, including ischaemia, Alzheimer's disease, neuroprotection and analgesia ("Neuronal Voltage-Sensitive Calcium Channels" *Drug News & Perspectives*, 1994, 7, 261–268). N-Type neuronal calcium channels have also been found to be involved in the release of various neurotransmitters and therefore, compounds that bind to N-type calcium channels may also be useful in various disease states characterized by abnormal neurotransmitter release, for example, anxiety, schizophrenia, Parkinson's disease and migraine.

Patent application EP 0 202 654 discloses 5-carboxy-1,4-dihydropyrimidine derivatives of general structure:

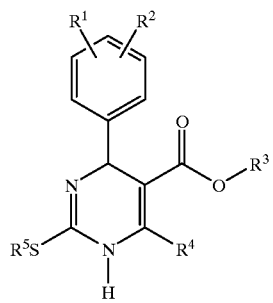

as cardiovascular agents, particularly, by virtue of their vasodilator activity, as antihypertensive agents. These compounds are distinguished from the scope of the present application by virtue of the definition of the group $R^2$ and by their different pharmacological activity.

Patent application JP 62-267272 discloses dihydropyrimidines of general structure:

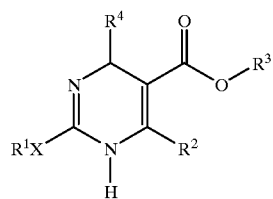

as agents for the treatment of circulation disorders. These compounds are distinguished from the scope of the present application by virtue of the definitions of groups $R^3$ and $R^4$, and by their different pharmacological activity.

DISCLOSURE OF THE INVENTION

According to the invention we provide a compound of formula (I)

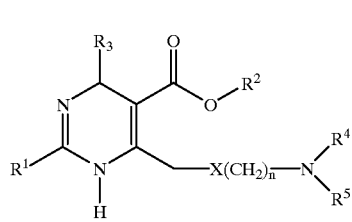

(I)

wherein:
  $R^1$ represents $SR^6$, $NR^6R^7$ or $OR^6$;
  $R^2$ represents alkyl C 1 to 6 or unsaturated alkyl C 2 to 6, either optionally including O or S, and which is substituted by a phenyl or a monocyclic heteroaryl ring, which aromatic ring is optionally substituted by one or more substituents independently selected from halogen, alkyl C 1 to 6 or alkoxy C 1 to 6;
  $R^3$ represents a monocyclic or bicyclic aromatic ring optionally incorporating one heteroatom selected from N, O or S, optionally substituted by one or more substituents independently selected from halogen, alkyl C 1 to 6, alkoxy C 1 to 6, cyano, trifluoromethyl, amino, hydroxy, nitro or carbomethoxy;
  $R^4$ and $R^5$ independently represent hydrogen, alkyl C 1 to 6, orbenzyl; or the group $NR^4R^5$ together represents piperidinyl, morpholinyl, 3,4-dehydropiperidinyl, thiomorpholinyl, pyrrolidinyl, N-methylpiperidinium, piperazinyl or piperazinyl further substituted at N-4 by alkyl C 1 to 6;
  $R^6$ and $R^7$ independently represent alkyl C 1 to 6 or cycloalkyl C 3 to 6, or benzyl, optionally substituted on the phenyl ring by alkyl C 1 to 6, alkoxy C 1 to 6 or halogen;
  X represents O, S or $NR^8$;
  $R^8$ represents hydrogen or alkyl C 1 to 6;
  and n represents an integer 2 to 4;
  and optical isomers and racemates thereof and pharmaceutically acceptable salts thereof.

Examples of said "monocyclic or bicyclic aromatic ring optionally incorporating one heteroatom selected from N, O or S" include, but are not limited to, phenyl; 1- and 2-naphthyl; 2-, 3- and 4-pyridyl; 2- and 3-thienyl; 2- and 3-furyl;quinolyl; isoquinolyl; indolyl; benzothienyl and benzofuryl.

Unless otherwise indicated, the term "alkyl C1 to 6" referred to herein denotes a straight or branched chain alkyl group having from 1 to 6 carbon atoms or a cyclic alkyl group having from 3 to 6 carbon atoms. Examples of such groups include methyl, ethyl, n-propyl, i-propyl, n-butyl, i-butyl, t-butyl, cyclopentyl and cyclohexyl.

Unless otherwise indicated, the term "unsaturated alkyl C2 to 6" referred to herein denotes a straight or branched chain alkyl group having from 2 to 6 carbon atoms and including one double bond or one triple bond or a cyclic alkyl group having from 3 to 6 carbon atoms and including one double bond. Examples of such groups include ethenyl, ethynyl, 1- and 2-propenyl, 1- and 2-propynyl, 2-methyl-2-propenyl, 2-butenyl, 2-butynyl, cyclopentenyl and cyclohexenyl.

Unless otherwise indicated, the term "alkoxy C1 to 6" referred to herein denotes a straight or branched chain alkoxy group having from 1 to 6 carbon atoms. Examples of such groups include methoxy, ethoxy, n-propoxy, i-propoxy, n-butoxy, i-butoxy, s-butoxy and t-butoxy.

Unless otherwise indicated, the term "halogen" referred to herein denotes fluorine, chlorine, bromine and iodine.

1,4-Dihydropyrimidines such as compounds of formula (I) may exist to a greater or lesser extent in the tautomeric 3,4-dihydro form (Ia):

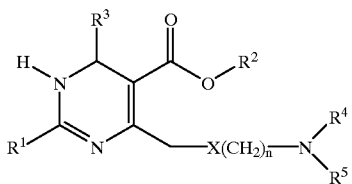

(Ia)

Wherever compounds are shown or named as 1,4-dihydropyrimidines, it is to be understood that both the 1,4-dihydro and 3,4-dihydro tautomers and mixtures thereof are included within the scope of the invention.

Preferred compounds of the invention are compounds of formula (I) wherein:

$R^1$ represents $SR^6$ and $R^6$ represents alkyl C 1 to 6;

$R^2$ represents 3-phenylpropyl or 3-(1-phenoxy)propyl, optionally substituted on the phenyl ring by halogen;

$R^3$ represents a 4-substituted phenyl, optionally further substituted in the 2- or 3-position, or 2-quinolyl;

$R^4$ and $R^5$ independently represent alkyl C 1 to 6, or the group $NR^4R^5$ together represents piperidinyl, pyrrolidinyl or piperazinyl further substituted at N-4 by alkyl C 1 to 6;

X represents O;

and n is 2.

Particularly preferred compounds of the invention include:

3-phenylpropyl 4-(3,4-dichlorophenyl)-2-methoxy-6-[(2-(1-piperidinyl)ethoxy)methyl]-1,4-dihydropyrimidine-5-carboxylate, 3-phenylpropyl 4-(3,4-dichlorophenyl)-2-ethylthio-6-[(2-(1-piperidinyl)ethoxy)methyl]-1,4-dihydropyrimidine-5-carboxylate, 3-phenylpropyl 2-methylthio-4-(2-naphthyl)-6-[(2-(1-piperidinyl)ethoxy)methyl]-1,4-dihydropyrimidine-5-carboxylate, 3-phenylpropyl 2-methylthio-6-[(2-(1-piperidinyl)ethoxy)methyl]-4-(2-quinolyl)-1,4-dihydropyrimidine-5-carboxylate, 3-phenylpropyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3,5-dichlorophenyl)-2-methylthio-6-[(2-(1-piperidinyl)ethoxy)methyl]-1,4-dihydropyrimidine-5-carboxylate, 3-phenylpropyl 2-methylthio-4-(4-nitrophenyl)-6-[(2-(1-piperidinyl)ethoxy)methyl]-1,4-dihydropyrimidine-5-carboxylate, 2-(4-chlorophenoxy)ethyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(4-chlorophenyl)-2-methylthio-6-[(2-(1-piperidinyl)ethoxy)methyl]-1,4-dihydropyrimidine-5-carboxylate, 3-phenylpropyl 4-(3,5-bis(trifluoromethyl)phenyl)-2-methylthio-6-[(2-(1-piperidinyl)ethoxy)methyl]-1,4-dihydropyrimidine-5-carboxylate, 3-phenylpropyl 4-(4-methylphenyl)-2-methylthio-6-[(2-(1-piperidinyl)ethoxy)methyl]-1,4-dihydropyrimidine-5-carboxylate, 3-phenylpropyl 4-(4-cyanophenyl)-2-methylthio-6-[(2-(1-piperidinyl)ethoxy)methyl]-1,4-dihydropyrimidine-5-carboxylate, 3-phenylpropyl (+)-4-(3,4-dichlorophenyl)-2-methylthio-6-[(2-(1-piperidinyl)ethoxy)methyl]-1,4-dihydropyrimidine-5-carboxylate, 3-phenylpropyl 4-(4-methyl-3-nitrophenyl)-2-methylthio-6-[(2-(1-piperidinyl)ethoxy)methyl]-1,4-dihydropyrimidine-5-carboxylate, 3-phenylpropyl 4-(4-chloro-3-nitrophenyl)-2-methylthio-6-[(2-(1-piperidinyl)ethoxy)methyl]-1,4-dihydropyrimidine-5-carboxylate, 3-phenylpropyl 4-(4-ethylphenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6-[(2-(N,N-diethylamino)ethylthio)methyl]-2-methylthio-1,4-dihydropyrirnidine-5-carboxylate, 3-phenylpropyl 4-(4-iodophenyl)-2-methylthio-6-[(2-(1-piperidinyl)ethoxy)methyl]-1,4-dihydropyrimidine-5-carboxylate, 3-phenylpropyl 4-(4-bromophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6[(2-(N,N-diethylamino)ethoxy)methyl]-2-methylthio-1,4-dihydropyrimidine-5-carboxylate, 3-phenoxypropyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(4-methoxycarbonylphenyl)-2-methylthio-6-[(2-(1-piperidinyl)ethoxy)methyl]-1,4-dihydropyrimidine-5-carboxylate, 3-phenylpropyl 4-(4-methoxyphenyl)-2-methylthio-6-[(2-(1-piperidinyl)ethoxy)methyl]-1,4-dihydropyrimidine-5-carboxylate, 3-phenylpropyl 2-methylthio-6-[(2-(1-piperidinylethoxy)methyl]-4-(2-thienyl)-1,4-dihydropyrimidine-5-carboxylate, 3-phenylpropyl 2-methylthio-4-phenyl-6-[(2-(1-piperidinyl)ethoxy)methyl]-1,4-dihydropyrimidine-5-carboxylate, 3-phenylpropyl 4-(3,4-dichlorophenyl)-2-dimethylamino-6-[(2-(1-piperidinyl)ethoxy)methyl]-1,4-dihydropyrimidine-5-carboxylate, 2-(3-methylphenoxy)ethyl 4-(3,4-dichlorophenyl)-2-methylthio-6-[(2-(1-piperidinyl)ethoxy)methyl]-1,4-dihydropyrimidine-5-carboxylate, 2-phenoxyethyl 4-(3,4-dichlorophenyl)-2-methylthio-6-[(2-(1-piperidinyl)ethoxy)methyl]-1,4-dihydropyrimidine-5-carboxylate, 3-(3,4-dimethoxyphenyl)propyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3-chlorophenyl)-2-methylthio-6-[(2-(1-piperidinyl)ethoxy)methyl]-1,4-dihydropyrimidine-5-carboxylate, 2-phenethyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-2-(4-methoxyphenyl)methylthio-6-[(2-(1-piperidinyl)ethoxy)methyl]-1,4-dihydropyrimidine-5-carboxylate, 3-phenylpropyl 4-(4-isopropylphenyl)-2-methylthio-6-[(2-(1-piperidinyl)ethoxy)methyl]-1,4-dihydropyrimidine-5-carboxylate, 3-phenylpropyl 4-(3,4-dichlorophenyl)-2-methylthio-6[(4-(1-piperidinyl)butyloxy)methyl]-1,4-dihydropyrimidine-5-carboxylate, 3-phenylpropyl 2-methylthio-6-[(2-(1-piperidinyl)ethoxy)methyl]-4-(4-trifluoromethylphenyl)-1,4-dihydropyrimidine-5-carboxylate, 3-phenylpropyl 2-methylthio-4-(3-nitrophenyl)-6-[(2-(1-piperidinyl)ethoxy)methyl]-1,4-dihydropyrimidine-5-carboxylate, 3-(4-methoxyphenyl)propyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6-[(2-(N,N-dimethylamino)ethoxy)methyl]-2-methylthio-1,4-dihydropyrimidine-5-carboxylate, 3-phenylpropyl 6-(2-aminoethoxymethyl)-4-(3,4-dichlorophenyl)-2-methylthio-1,4-dihydropyrimidine-5-carboxylate, 3-phenylpropyl 4-(3,4-dichlorophenyl)-2-methylthio-6[(2-(4-morpholinyl)ethoxy)methyl]-1,4-dihydropyrimidine-5-carboxylate, 3-phenylpropyl (−)-4-(3,4-dichlorophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6-[(2-(N,N-diethylamino)ethylamino)methyl]-2-methylthio-1,4-dihydropyrimidine-5-carboxylate, 3-phenylpropyl 4-(3-hydroxy-4-nitrophenyl)-2-methylthio-6-[(2-(1-piperidinyl)ethoxy)methyl]-1,4-dihydropyrimidine-5-carboxylate, 3-phenylpropyl 4-(4-hydroxy-3-nitrophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-2-methylthio-6-[(2-(1-N-methylpiperidinium)ethoxy)methyl]-1,4-dihydropyrimidine-5-carboxylate chloride, and tautomers thereof and pharmaceutically acceptable salts thereof.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

According to the invention, we further provide a process for the preparation of compounds of formula (I), and optical isomers and racemates thereof and pharmaceutically acceptable salts thereof, which comprises:

(a) preparing a compound of formula (I) by reacting a corresponding compound of formula (II)

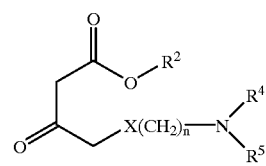
(II)

wherein $R^2$, $R^4$, $R^5$, X and n are as defined above
with a compound of formula (III) or an acid addition salt thereof

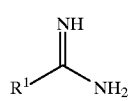
(III)

wherein $R^1$ is as defined above
and with a compound of formula (IV)

(IV)

wherein $R^3$ is as defined above;

(b) preparing a compound of formula (I) by reacting a corresponding compound of formula (V)

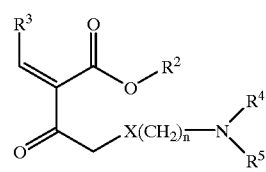
(V)

wherein $R^2$, $R^3$, $R^4$, $R^5$, X and n are as defined above
with a compound of formula (III) or an acid addition salt thereof

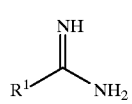
(III)

wherein $R^1$ is as defined above; or (c) preparing a compound of formula (I) by reacting a corresponding compound of formula (VI)

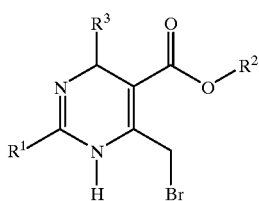
(VI)

wherein $R^1$, $R^2$ and $R^3$ are as defined above
with a compound of formula (VII)

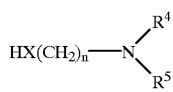
(VII)

wherein $R^4$, $R^5$, X and n are as defined above;

and where desired or necessary converting the resultant compound of formula (I), or another salt thereof, to a pharmaceutically acceptable salt thereof, or vice versa.

In process (a), the reaction will take place on stirring a mixture of compounds of formula (II), (III) and (IV) in a suitable solvent at a temperature between 15° and 150° C., preferably between 25° and 75° C., with or without addition of an acid or a base. Suitable solvents include tetrahydrofuran, dioxane, acetonitrile, N,N-dimethylformamide, ethanol or isopropanol, preferably N,N-dimethylformamide, ethanol or isopropanol. Sodium acetate, potassium carbonate and sodium hydrogen carbonate are preferred bases. The reaction time will depend inter alia on the solvent and the temperature used, and may be up to several days.

In process (b), the reaction will take place on stirring a mixture of compounds of formula (III) and (V) in a suitable solvent at a temperature between 15° and 150° C., preferably between 25° and 75° C., with or without addition of an acid or a base. Suitable solvents include tetrahydrofuran, dioxane, acetonitrile, N,N-dimethylformamide, ethanol or isopropanol, preferably N,N-dimethylformamide, ethanol or isopropanol. The reaction time will depend inter alia on the solvent and the temperature used, and may be up to several days.

In process (c), the reaction will take place on stirring a mixture of compounds of formula (VI) and (VII) in a suitable inert solvent such as tetrahydrofuran, dioxane, acetonitrile, N,N-dimethylformamide, ethanol or isopropanol.

Salts of compounds of formula (I) may be formed by reacting the free base or a salt, enantiomer, tautomer or protected derivative thereof, with one or more equivalents of the appropriate acid. The reaction may be carried out in a solvent or medium in which the salt is insoluble, or in a solvent in which the salt is soluble followed by subsequent removal of the solvent in vacuo or by freeze drying. Suitable solvents include, for example, water, dioxan, ethanol, isopropanol, tetrahydrofuran or diethyl ether, or mixtures thereof. The reaction may be a metathetical process or it may be carried out on an ion exchange resin.

Certain novel intermediates of formulae (II), (III), (IV), (V) and (VI) form another aspect of the invention.

Compounds of formula (II) may be formed by reaction of a compound of formula (VIII)

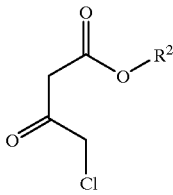
(VIII)

wherein $R^2$ is as defined above
with a compound of formula (VII) in a suitable solvent with or without the addition of a base. The choice of the solvent and the base will depend inter alia on the nature of the group X. Suitable solvents include ethers, tetrahydrofuran or N,N-dimethylformamide. Suitable bases include metal hydrides such as sodium hydride or potassium hydride, carbonates such as sodium carbonate or potassium carbonate, tertiary amines such as triethylamine or 1,8-diazabicyclo[5.4.0]undec-7-ene, preferably sodium hydride or potassium carbonate.

Compounds of formula (VIII) may be prepared by heating a compound of formula (IX)

$R^2$—OH (IX)

wherein $R^2$ is as defined above
with a compound of formula (X)

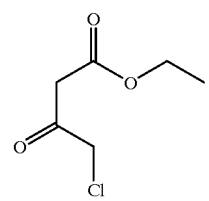
(X)

in an inert solvent such as toluene, benzene or dichloromethane. The use of toluene as solvent in conjunction with the azeotropic removal of ethanol represents a preferred procedure.

Alternatively, the order of the above steps may be varied such that compounds of formula (II) are formed by reaction of a compound of formula (X) with a compound of formula (VII), and then reaction of the product therefrom with a compound of formula (IX).

Compounds of formula (V) may be formed by reaction of compounds of formula (II) with compounds of formula (IV) under standard conditions known to one skilled in the art.

Compounds of formula (VI) may be made by bromination of a compound of formula (XI)

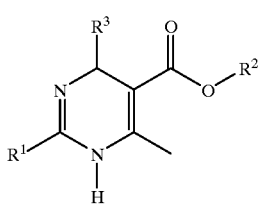
(XI)

using methods well known to one skilled in the art.

Compounds of formula (XI) can be made by condensation of a mixture of compounds of formula (III), (IV) and (XII)

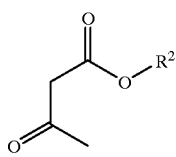

(XII)

wherein R² is as defined above under conditions similar to those used for the preparation of compounds of formula (I) according to process (a) above.

Compounds of formula (III), (IV), (VII), (IX), (X) and (XII) are either commercially available or may be prepared by methods known to one skilled in the art.

Intermediate compounds may be prepared as such or in protected form. In particular amine groups may be protected. Suitable protecting groups are described in the standard text "Protective Groups in Organic Synthesis", 2nd Edition (1991) by Greene and Wuts. Amine-protecting groups which may be mentioned include alkyloxycarbonyl such as t-butyloxycarbonyl, phenylalkyloxycarbonyl such as benzyloxycarbonyl, trifluoroacetate or phthaloyl. Deprotection will normally take place on treatment with aqueous base or aqueous acid, or, in the case of phthaloyl, with hydrazine.

Other syntheses of compounds of formula (II), (V), (VI) and (XI) will be readily apparent to one skilled in the art.

The compounds of the invention and intermediates may be isolated from their reaction mixtures, and if necessary further purified, by using standard techniques.

The compounds of formula (I) may exist in tautomeric, enantiomeric or diastereoisomeric forms, all of which are included within the scope of the invention. The various optical isomers may be isolated by separation of a racemic mixture of the compounds using conventional techniques such as fractional crystallisation or HPLC. Alternatively, the individual enantiomers may be made by reaction of the appropriate optically active starting materials under reaction conditions which will not cause racemisation.

Intermediate compounds may also exist in enantiomeric or tautomeric forms and may be used as purified enantiomers, diastereomers, racemates, tautomers or mixtures thereof.

Compounds of formula (I) are blockers of N-type neuronal calcium channels and as such are useful in the treatment or prophylaxis of disorders arising from a dysfunction of N-type neuronal calcium channels. While not being limited by theory, it is believed that blockers of N-type neuronal calcium channels will be useful in the treatment or prophylaxis of a range of CNS diseases. Thus, the utility of the compounds of the present invention is in the treatment or prophylaxis of cerebrovascular ischaemia, due to such conditions as stroke, head trauma, cardiac arrest, spinal cord injury, anoxia, hypoxia and cardiac surgery, particularly coronary artery bypass surgery;neurodegenerative disorders such as Alzheimer's disease, Parkinson's disease and AIDS-related dementia; pain, including nociceptive and neuropathic pain syndromes; cognitive or attention disorders; psychotic disorders, particularly schizophrenia; affective disorders such as anxiety and depression; and migraine.

Compounds of formula (I) are predicted to be particularly useful in the treatment or prophylaxis of cerebrovascular ischaemia, stroke, head trauma, pain, Alzheimer's disease and schizophrenia.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

Thus according to a further aspect of the invention we provide a compound of formula (I), or an optical isomer or racemate thereof or a pharmaceutically acceptable salt thereof, for use as a medicament.

According to another feature of the invention we provide the use of a compound of formula (I) or an optical isomer or racemate or tautomer thereof or a pharmaceutically acceptable salt thereof, in the manufacture of a medicament for the treatment or prophylaxis of the aforementioned diseases or conditions; and a method of treating, or reducing the risk of, one of the aforementioned diseases or conditions which comprises administering to a person suffering from or susceptible to such a disease or condition, a therapeutically effective amount of a compound of formula (I), or an optical isomer or racemate or tautomer thereof or a pharmaceutically acceptable salt thereof.

For the above mentioned therapeutic indications, the dosage administered will, of course, vary with the compound employed, the mode of administration and the treatment desired. However, in general, satisfactory results are expected to be obtained when the compounds are administered to a human at a daily dosage of between 0.5 mg and 2000 mg (measured as the active ingredient) per day, particularly at a daily dosage of between 2 mg and 500 mg.

The compounds of formula (I), and optical isomers and racemates thereof and pharmaceutically acceptable salts thereof, may be used on their own, or in the form of appropriate medicinal formulations. Administration may be by, but is not limited to, enteral (including oral, sublingual or rectal), intranasal, topical or parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988.

According to the invention, there is provided a pharmaceutical formulation comprising preferably less than 99% by weight, more preferably less than 80% by weight, and even more preferably less than 50% by weight, of a compound of formula (I), or an optical isomer or racemate thereof or a pharmaceutically acceptable salt thereof, in admixture with a pharmaceutically acceptable diluent or carrier.

We also provide a method of preparation of such a pharmaceutical formulation which comprises mixing the ingredients.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include: tablets, capsules and dragees; sustained release compositions include those in which the active ingredient is bound to an ion exchange resin which is optionally coated with a diffusion barrier to modify the release properties of the resin.

The pharmacological activity of the compounds of the present invention may be assessed using one or more of the following assays:

1) Assay for affinity at N-type calcium channels—[$^{125}$I]-MVIIA binding to rat synaptic membranes.

Preparation of Synaptic Membranes

Rat brains minus cerebella were homogenized in ice-cold 0.32M sucrose containing protease inhibitors (SPI: 1 μM leupeptin; 2 μM pepstatin; 1.0 mM EGTA; 1 mM EDTA). The homogenate was centrifuged at 1000 g for 15 minutes at 4° C. The resulting supernatant was centrifuged at 12,000 g for 15 minutes at 4° C. The pellets were washed by recentrifugation, resuspended in SPI buffer and layered over a discontinuous (0.6M/0.8M/1.2M) sucrose gradient in Beckman Ultraclear Ultracentrifuge tubes. After centrifugation at 140,000 g for 75 minutes at 4° C., the 0.8M layers including the 0.8/1.2M interfaces were collected, pooled and diluted to 0.32M sucrose with ice cold water containing protease inhibitors. This suspension was centrifuged at 15,000 g for 15 minutes at 4° C. The pellets were resuspended in ice cold water containing protease inhibitors and frozen at −140° C. Membranes were harvested from thawed suspensions by 3-fold dilution with ice cold water containing protease inhibitors, polytron homogenization, and centrifugation at 41,000 g for 20 minutes at 4° C. The pellets were resuspended in phosphate buffered saline containing protease inhibitors and stored in aliquots at −70° C. until used.

Assay

Compounds in 20 μl DMSO were added to 100 μL buffer (75 mM NaCl, 0.1 mM EDTA, 0.1 mM EGTA, 0.1% bovine serum albumin, 100 μg/ml chymostatin, 0.35 μg/ml aprotinin, 10 μg/ml leupeptin, 20 mM HEPES, pH 7.0) containing 18 pM [$^{125}$I]-MVIIA. The reaction was started by adding 380 μL buffer containing 2 μg synaptic membrane protein. After incubation at room temperature for 1 hour, bound radioactivity was recovered by filtration onto Packard GF/C Unifilter plates (presoaked in 0.3% polyethylenimine containing 100 μM neomycin sulfate). After washing, 25 μl MicroScint scintillation fluid was added to each filter well and radioactivity was measured in a Packard TopCount scintillation counter. Nonspecific binding was measured in the presence of 100 μM neomycin sulfate.

In the screen for affinity for N-type calcium channels, compound activity is expressed as $IC_{50}$ (the concentration of drug substance which gives 50% binding inhibition in the assay). is $IC_{50}$ values for test compounds were initially estimated from the inhibiting activity of 1, 10 and 100 μM solutions of the compounds. Compounds that inhibited the binding by at least 50% at 10 μM were re-tested using more appropriate concentrations so that an $IC_{50}$ could be determined.

2) In vitro method for assaying antagonism of N-type voltage operated calcium channels SHSY5Y cells, a human neuroblastoma line, were cultured in 96 well microplates and differentiated with retinoic acid. The cells were loaded with Fluo-3/AM, a calcium fluorescent indicator, and treated with appropriate concentrations of test compound in the presence of 1 μM nifedipine for 30 minutes. Calcium channels were activated by depolarizing the cells by the addition of KCl (75 mM final concentration). Peak fluorescence intensity resulting from increased intracellular levels of calcium was measured simultaneously in all wells using a Fluorescence Imaging Plate Reader. The decrease in peak fluorescence intensity relative to untreated control cells was used to determine calcium channel antagonism. $IC_{50}$ values were generated for test compounds as an index of antagonist potency.

3) Electrophysiological assay of N-type calcium channel currents

Superior cervical ganglion cells were isolated from 2 week old rat pups using a modification of the method described by K. J. Swartz, *Neuron*, 1993, 11, 305–320. The cells were maintained in Leibovitz L-15 buffer on ice, plus oxygen for up to 8 hours (no bubbles).

Whole-cell patch clamp recordings were performed in bath buffer (115 mM NaCl; 10 mM D-glucose; 10 mM HEPES; 4.9 mM KCl; 2.5 mM $MgCl_2$; 10 mM TEACl; 0.5 μM TTX; 10 mM $BaCl_2$; pH 7.4) with pipette buffer (130 mM CsCl; 10 mM EGTA; 20 mM HEPES; 5 mM D-glucose; 3 mM ATP-$Na_2$; 5 mM $MgCl_2$-ATP; 0.25 mM GTP-Li; pH 7.1 with CsOH). Channels were elicited to open by voltage pulses to 0 mV from a holding potential of −80 mV. Test compounds were dissolved in DMSO at 1000 times their final concentrations and then diluted in bath buffer. Currents were measured in a flow-through chamber before and after application of the test compound. Percent inhibition was calculated from the difference in these two measurements.

The compounds of Examples 1 to 44 below showed significant activity when tested in one or more of the above assays. This activity at N-type neuronal calcium channels indicates that such compounds are predicted to show particularly useful therapeutic activity.

The invention is illustrated by the following non-limiting examples:

PREPARATION 1

3-Phenylpropyl 4-chloroacetoacetate

A solution of ethyl 4-chloroacetoacetate (134 g, 815 mmol) and 3-phenyl-1-propanol (111 mL, 821 mmol) was heated in toluene, with azeotropic removal of ethanol, for 4 h. The solution was allowed to cool with stirring for 18 h and was then concentrated to give the title compound (214 g). Electrospray $MS^m/z$ 219 [M-Cl+H]$^+$.

PREPARATION 2

3-Phenylpropyl 4-(2-(1-piperidinyl)ethoxy)acetoacetate 2-(1-Piperidinyl)ethanol (15 mL, 113 mmol) in THF (50 mL) was added dropwise to a suspension of sodium hydride (7 g, 175 mmol) in THF (200 mL) at 0° C. The mixture was then stirred for 1 h at room temperature, cooled to 0° C., 3-phenylpropyl 4-chloroacetoacetate (22 mL, 103 mmol) in THF (50 mL) was added dropwise and the reaction mixture was then stirred for 18 h whilst warming to room temperature. 1N Hydrochloric acid was added until the mixture was acidic and the aqueous layer was then separated. The organic layer was extracted twice more with 1N hydrochloric acid. The combined acid layers were made basic to pH 8 with sodium hydrogen carbonate and extracted with chloroform. The combined extracts were washed with brine, dried and evaporated to give the title compound (24 g) as an oil. Electrospray $MS^m/z$ 348 [M+H]$^+$.

Following the general procedure of Preparation 2 but using 4-(1-piperidinyl)butanol, the following compound was synthesised:

3-phenylpropyl 4-(4-(1-piperidinyl)butyloxy) acetoacetate. Electrospray $MS^m/z$ 376 [M+H]$^+$.

PREPARATION 3

3-Phenylpropyl 4-(2-(N,N-diethylamino)ethoxy) acetoacetate

N,N-Diethylaminoethanol (7.49 mL, 56.6 mmol) in THF (25 mL,) was added dropwise to a suspension of sodium hydride (3.5 g, 87.5 mmol) in THF (100 mL) at 0° C. The mixture was then stirred for 30 minutes at room temperature, cooled to 0° C., 3-phenylpropyl 4-chloroacetoacetate (11.10 mL, 51.5 mmol) in THF (25 mL) was added dropwise and the reaction mixture was then stirred for 18 h whilst warming to room temperature. 1N Hydrochloric acid was added until the mixture was acidic and the aqueous layer was then separated. The organic layer was extracted twice more with 1N hydrochloric acid. The combined acid layers were washed two times with ethyl acetate and then made basic to pH 8 with sodium hydrogen carbonate and extracted with chloroform three times. The combined extracts were washed with brine, dried and evaporated to give the title compound (16.3 g) as an oil. Electrospray MS$^m$/z 336 [M+H]$^+$.

Following the general procedure for Preparation 3, the following compounds were synthesized:

3-Phenylpropyl 4-(2-(N,N-dimethylamino)ethoxy) acetoacetate. Electrospray MS$^m$/z 308 [M+H]$^+$.

3-Phenylpropyl 4-(2-(1-morpholinyl)ethoxy) acetoacetate. Electrospray MS$^m$/z 350 [M+H]$^+$.

PREPARATION 4

3-Phenylpropyl 4-(2-(2-(1,3-dihydro-1,3-dioxo-2H-isoindolyl))ethoxy)acetoacetate 2-(2-(1,3-Dihydro-1,3-dioxo-2H-isoindolyl))ethanol (7.1 g, 37.5 mmol) was added to a suspension of sodium hydride (1.5 g, 37.5 mmol) in THF with stirring under a nitrogen atmosphere. The mixture was stirred for 1 h at room temperature, cooled to 0° C., ethyl 4-chloroacetoacetate (2.5 mL, 18.7 mmol) in THF was added dropwise and the reaction mixture was stirred for 48 h whilst warming to room temperature. 1N Hydrochloric acid was added until the mixture was acidic, the aqueous layer was separated and the organic phase was extracted twice more with 1N hydrochloric acid. The combined acid layers were made basic to pH 8 with sodium hydrogen carbonate and extracted with chloroform. The combined extracts were washed with brine, dried and evaporated to give ethyl 4-(2-(2-( 1,3-dihydro-1, 3-dioxy-2H-isoindolyl))ethoxy)acetoacetate (3 g) as an oil. Electrospray MS$^m$/z 320 [M+H]$^+$.

This oil was combined with 3-phenyl-1-propanol (1.35 mL, 10 mmol) and heated in toluene, with azeotropic removal of ethanol, for 4 h. The solution was allowed to cool with stirring for 18 h and was then concentrated to give the title compound as a light tan coloured oil. Electrospray MS$^m$/z 410 [M+H]$^+$.

Following the general procedure for Preparation 4, the following compounds were synthesized:

2-(3-Methylphenoxy)ethyl 4-(2-(1-piperidinyl)ethoxy) acetoacetate. Electrospray MS$^m$/z 364 [M+H]$^+$.

2-(4-Chlorophenoxy)ethyl 4-(2-(1-piperidinyl)ethoxy) acetoacetate. Electrospray MS$^m$/z 384 [M+H]$^+$.

2-Phenoxyethyl 4-(2-(1-piperidinyl)ethoxy)acetoacetate. Electrospray MS$^m$/z 350 [M+H]$^+$.

2-Phenylethyl 4-(2-(1-piperidinyl)ethoxy)acetoacetate. Electrospray MS$^m$/z 334 [M+H]$^+$.

3-(4-Methoxyphenyl)propyl 4-(2-(1-piperidinyl)ethoxy) acetoacetate. Electrospray MS$^m$/z 378 [M+H]$^+$.

3-(3,4-Dimethoxyphenyl)propyl 4-(2-(1-piperidinyl) ethoxy)acetoacetate. Electrospray MS$^m$/z 408 [M+H]$^+$.

PREPARATION 5

2-(4-Methoxybenzyl)isothiourea

To a mixture of thiourea (3.8 g, 50.0 mmol) in tetrahydrofuran (30 mL) was added dropwise 4-methoxybenzyl chloride (8.0 g, 51.1 mmol) and the reaction mixture was stirred at room temperature for 2 h before heating to reflux for 4 h. After the reaction was stirred at room temperature for 18 h the product was isolated from ether to yield the title compound (11.46 g). Electrospray MS$^m$/z 197 [M+H]$^+$.

PREPARATION 6

3-Phenylpropyl 4-(2-(N,N-diethylamino)ethylthio) acetoacetate 2-(N,N-Diethylamino)ethylthiol (2.80 g, 16.5 mmol) and potassium carbonate (4.56 g, 33.0 mmol) were stirred at room temperature in THF (50 mL) for 1 h. This mixture was then cooled to 0° C., and 3-phenylpropyl 4-chloroacetoacetate (3.23 mL, 15.0 mmol) in THF (15 mL) was added dropwise and the reaction mixture was then stirred for 18 h whilst warming to room temperature. The potassium carbonate was removed by filtration and the filtrate was evaporated to give the title compound (5.71 g) as an oil. Electrospray MS$^m$/z 352 [M+H]$^+$.

EXAMPLE 1

3-Phenylpropyl 4-(3,4-dichlorophenyl)-2-methylthio-6-[(2-(1-piperidinyl)ethoxy)methyl]-1,4-dihydropyrimidine-5-carboxylate A mixture of 3-phenylpropyl 4-(2-(1-piperidinyl)ethoxy) acetoacetate (10.6 g, 30.6 mmol), 3,4-dichlorobenzaldehyde (5.9 g, 34.0 mmol), 2-methyl-2-thiopseudourea sulfate (6.15 g, 22.1 mmol) and sodium acetate (2.78 g, 34.0 mmol) was stirred in N,N-dimethylformamide (50 mL) for 4 days at room temperature, then heated to 60° C. for 24 h. The DMF was removed in vacuo and ethyl acetate was added to the residue. The precipitate was removed by filtration and the filtrate was washed with water, sodium hydrogen carbonate solution and brine, dried and evaporated to yield an oil. This oil was further purified by flash chromatography to give the title compound (1.3 g) as an oil. The oil can be converted into a mono or dihydrochloride salt, by dissolution in ether and addition of one or two equivalents of hydrogen chloride. Electrospray MS$^m$/z 576/578 [M+H]$^+$.

Following the general procedure for Example 1 but using the appropriate aromatic aldehyde, the compounds of Examples 2 to 24 were synthesized:

EXAMPLE 2

3-Phenylpropyl 4-(4-methoxycarbonylphenyl)-2-methylthio-6-[(2-(1-piperidinyl)ethoxy)methyl]-1,4-dihydropyrimidine-5-carboxylate Electrospray MS$^m$/z 566 [M+H]$^+$.

EXAMPLE 3

3-Phenylpropyl 2-methylthio-4-(2-naphthyl)-6-[(2-(1-piperidinyl)ethoxy)methyl]-1,4-dihydropyrimidine-5-carboxylate Electrospray MS$^m$/z 558 [M+H]$^+$.

EXAMPLE 4

3-Phenylpropyl 2-methylthio-6-[(2-(1-piperidinyl)ethoxy) methyl]-4-(2-guinolyl)-1,4-dihydropyrimidine-5-carboxylate Electrospray MS$^m$/z 559 [M+H]$^+$.

EXAMPLE 5

3-Phenylpropyl 4-(4-methoxyphenyl)-2-methylthio-6-[(2-(1-piperidinyl)ethoxy)methyl]-1,4-dihydropyrimidine-5-carboxylate Electrospray MS$^m$/z 538 [M+H]$^+$.

EXAMPLE 6

3-Phenylpropyl 2-methylthio-6-[(2-(1-piperidinyl)ethoxy) methyl]-4-(2-thienyl)-1,4-dihydropyrimidine-5-carboxylate Electrospray MS$^m$/z 514 [M+H]$^+$.

EXAMPLE 7
3-Phenylpropyl 2-methylthio-4-phenyl-6-[(2-(1-piperidinyl)ethoxy)methyl]-1,4-dihydropyrimidine-5-carboxylate Electrospray MS$^m$/z 508 [M+H]$^+$.

EXAMPLE 8
3-Phenylpropyl 4-(3,5-dichlorophenyl)-2-methylthio-6-[(2-(1-piperidinyl)ethoxy)methyl]-1,4-dihydropyrimidine-5-carboxylate Electrospray MS$^m$/z 576/578 [M+H]$^+$.

EXAMPLE 9
3-Phenylpropyl 2-methylthio-4-(4-nitrophenyl)-6-[(2-(1-piperidinyl)ethoxy)methyl]-1,4-dihydropyrimidine-5-carboxylate Electrospray MS$^m$/z 553 [M+H]$^+$.

EXAMPLE 10
3-Phenylpropyl 4-(4-chlorophenyl)-2-methylthio-6-[(2-(1-piperidinyl)ethoxy)methyl]-1,4-dihydropyrimidine-5-carboxylate Electrospray MS$^m$/z 542 [M+H]$^+$.

EXAMPLE 11
3-Phenylpropyl 4-(3-chlorophenyl)-2-methylthio-6-[(2-(1-piperidinyl)ethoxy)methyl]-1,4-dihydropyrimidine-5-carboxylate Electrospray MS$^m$/z 542 [M+H]$^+$.

EXAMPLE 12
3-Phenylpropyl 4-(315-bis(trifluoromethyl)phenyl)-2-methylthio-6-[(2-(1-piperidinyl)ethoxy)methyl]-1,4-dihydropyrimidine-5-carboxylate Electrospray MS$^m$/z 644 [M+H]$^+$.

EXAMPLE 13
3-Phenylpropyl 4-(4-methylphenyl)-2-methylthio-6-[(2-(1-piperidinyl)ethoxy)methyl]-1,4-dihydropyrimidine-5-carboxylate Electrospray MS$^m$/z 522 [M+H]$^+$.

EXAMPLE 14
3-Phenylpropyl 4-(4-isopropylphenyl)-2-methylthio-6-[(2-(1-piperidinyl)ethoxy)methyl]-1,4-dihydropyrimidine-5-carboxylate Electrospray MS$^m$/z 550 [M+H]$^+$.

EXAMPLE 15
3-Phenylpropyl 4-(3-hydroxy-4-nitrophenyl)-2-methylthio-6-[(2-(1-piperidinyl)ethoxy)methyl]-1,4-dihydropyrimidine-5-carboxylate Electrospray MS$^m$/z 569 [M+H]$^+$.

EXAMPLE 16
3-Phenylpropyl 2-methylthio-6-[(2-(1-piperidinyl)ethoxy)methyl]-4-(4-trifluoromethylphenyl)-1,4-dihydropyrimidine-5-carboxylate Electrospray MS$^m$/z 546 [M+H]$^+$.

EXAMPLE 17
3-Phenylpropyl 2-methylthio-4-(3-nitrophenyl)-6-[(2-(1-piperidinyl)ethoxy)methyl]-1,4-dihydropyrimidine-5-carboxylate Electrospray MS$^m$/z 587 [M+H]$^+$.

EXAMPLE 18
3-Phenylpropyl 4-(4-cvanophenyl)-2-methylthio-6-[(2-(1-piperidinyl)ethoxy)methyl]-1,4-dihydropyrimidine-5-carboxylate Electrospray MS$^m$/z 553 [M+H]$^+$.

EXAMPLE 19
3-Phenylpropyl 4-(4-methyl-3-nitrophenyl)-2-methylthio-6-[(2-(1-piperidinyl)ethoxy)methyl]-1,4-dihydropyrimidine-5-carboxylate Electrospray MS$^m$/z 576 [M+H]$^+$.

EXAMPLE 20
3-Phenylpropyl 4-(4-chloro-3-nitrophenyl)-2-methylthio-6-[(2-(1-piperidinyl)ethoxy)methyl]-1,4-dihydropyrimidine-5-carboxylate Electrospray MS$^m$/z 587 [M+H]$^+$.

EXAMPLE 21
3-Phenylpropyl 4-(4-ethylphenyl)-2-methylthio-6-[(2-(1-piperidinyl)ethoxy)methyl]-1,4-dihydropyrimidine-5-carboxylate Electrospray MS$^m$/z 536 [M+H]$^+$.

EXAMPLE 22
3-Phenylpropyl 4-(4-iodophenyl)-2-methylthio-6-[(2-(1-piperidinyl)ethoxy)methyl]-1,4-dihydropyrimidine-5-carboxylate Electrospray MS$^m$/z 634 [M+H]$^+$.

EXAMPLE 23
3-Phenylpropyl 4-(4-bromophenyl)-2-methylthio-6-[(2-(1-piperidinyl)ethoxy)methyl]-1,4-dihydropyrimidine-5-carboxylate Electrospray MS$^m$/z 586/588 [M+H]$^+$.

EXAMPLE 24
3-Phenylpropyl 4-(4-hydroxy-3-nitrophenyl)-2-methylthio-6-[(2-(1-piperidinyl)ethoxy)methyl]-1,4-dihydropyrimidine-5-carboxylate Electrospray MS$^m$/z 569 [M+H]$^+$.

EXAMPLE 25
3-Phenylpropyl 4-(3,4-dichlorophenyl)-2-methoxy-6-[(2-(1-piperidinyl)ethoxy)methyl]-1,4-dihydropyrimidine-5-carboxylate A mixture of 3-phenylpropyl 4-(2-(1-piperidinyl)ethoxy) acetoacetate (1.0 g, 2.88 mmol), 3,4-dichlorobenzaldehyde (0.60 g, 3.45 mmol), 2-methyl-2-pseudourea sulfate (0.89 g, 5.17 mmol) and sodium hydrogen carbonate (1.16 g, 13.8 mmol) was stirred in N,N-dimethylformamide (10 mL) for 8 days at room temperature. The DMF was removed in vacuo and ethyl acetate was added to the residue. The precipitate was removed by filtration and the filtrate was washed with water, sodium hydrogen carbonate solution and brine, dried and evaporated to yield an oil. This oil was further purified by flash chromatography to give the title compound (57.2 mg) as an oil. Electrospray MS$^m$/z 560/562 [M+H]$^+$.

Following the general procedure for Example 1, but using the appropriate acetoacetate ester, the compounds of Examples 26 to 33 were synthesised:

EXAMPLE 26
3-Phenylpropyl 4-(3,4-dichlorophenyl)-2-methylthio-6-[(4-(1-piperidinyl)butyloxy)methyl]-1,4-dihydropyrimidine-5-carboxylate Electrospray MS$^m$/z 604/606 [M+H]$^+$.

EXAMPLE 27
3-Phenoxypropyl 4-(3,4-dichlorophenyl)-2-methylthio-6-[(2-(1-piperidinyl)ethoxy)methyl]-1,4-dihydropyrimidine-5-carboxylate Electrospray MS$^m$/z 592/594 [M+H]$^+$.

EXAMPLE 28
2-(3-Methylphenoxy)ethyl 4-(3,4-dichlorophenyl)-2-methylthio-6-[(2-(1-piperidinyl)ethoxy)methyl]-1,4-dihydropyrimidine-5-carboxylate Electrospray MS$^m$/z 592/594 [M+H]$^+$.

EXAMPLE 29
2-Phenoxyethyl 4-(3,4-dichlorophenyl)-2-methylthio-6-[(2-(1-piperidinyl)ethoxy)methyl]-1,4-dihydropyrimidine-5-carboxylate Electrospray MS$^m$/z 578/580 [M+H]$^+$.

EXAMPLE 30
3-(3,4-Dimethoxyphenyl)propyl 4-(3,4-dichlorophenyl)-2-methylthio-6-[(2-(1-piperidinyl)ethoxy)methyl]-1,4-dihydropyrimidine-5-carboxylate Electrospray MS$^m$/z 636/638 [M+H]$^+$.

EXAMPLE 31
2-(4-Chlorophenoxy)ethyl 4-(3,4-dichlorophenyl)-2-methylthio-6-[(2-(1-piperidinyl)ethoxy)methyl]-1,4-dihydropyrimidine-5-carboxylate Electrospray MS$^m$/z 612/614 [M+H]$^+$.

EXAMPLE 32
2-Phenethyl 4-(3,4-dichlorophenyl)-2-methylthio-6-[(2-(1-piperidinyl)ethoxy)methyl]-1,4-dihydropyrimidine-5-carboxylate Electrospray MS$^m$/z 562/564 [M+H]$^+$.

EXAMPLE 33
3-(4-Methoxyphenyl)propyl 4-(3,4-dichlorophenyl)-2-methylthio-6-[(2-(1-piperidinyl)ethoxy)methyl]-1,4-dihydropyrimidine-5-carboxylate Electrospray MS$^m$/z 606/608 [M+H]$^+$.

Following the general procedure for Example 1, but using the appropriate thiourea derivative, the compound of Example 34 was synthesised:

EXAMPLE 34
3-Phenylpropyl 4-(3,4-dichlorophenyl)-2-ethylthio-6-[(2-(1-piperidinyl)ethoxy)methyl]-1,4-dihydropyrimidine-5-carboxylate Electrospray MS$^m$/z 590/592 [M+H]$^+$.

EXAMPLE 35
3-Phenylpropyl 4-(3,4-dichlorophenyl)-2-(4-methoxyphenyl)methylthio-6-[(2-(1-piperidinyl)ethoxy)methyl]-1,4-dihydropyrimidine-5-carboxylate A mixture of 3-phenylpropyl 4-(2-(1-piperidinyl)ethoxy)acetoacetate (1.0 g, 2.88 mmol), 3,4-dichlorobenzaldehyde (0.60 g, 3.45 mmol), 2-(4-methoxybenzyl)isothiourea (0.80 g, 3.45 mmol) and sodium hydrogen carbonate (0.29 g, 3.45 mmol) was stirred in N,N-dimethylformamide (10 mL) for 6 days at room temperature, then heated to 50° C. for 7 days. The DMF was removed in vacuo and ethyl acetate was added to the residue. The precipitate was removed by filtration and the filtrate was washed with water, sodium hydrogen carbonate solution and brine, dried and evaporated to yield an oil. This oil was further purified by flash chromatography to give the title compound (0.50 g) as an oil. The oil can be converted into a mono or dihydrochloride salt, by dissolution in ether and addition of one or two equivalents of hydrogen chloride. Electrospray MS$^m$/z 682/684 [M+H]$^+$.

EXAMPLE 36
3-Phenylpropyl 4-(3,4-dichlorophenyl)-2-dimethylamino-6-[(2-(1-piperidinyl)ethoxy)methyl]-1,4-dihydropyrimidine-5-carboxylate A mixture of 3-phenylpropyl 4-(2-(1-piperidinyl)ethoxy)acetoacetate, (0.83 g, 2.4 mmol), 3,4-dichlorobenzaldehyde (0.63 g, 3.6 mmol), 1,1-dimethylguanidine sulfate (0.65 g, 2.4 mmol) and sodium methoxide (0.13 g, 2.4 mmol) was stirred in N,N-dimethylformamide (25 mL) for 24 h at room temperature. The DMF was removed in vacuo and the residue was purified by RP-HPLC to yield an oily solid (220 mg). The oily solid can be converted into a mono or dihydrochloride salt, by dissolution in ether and addition of one or two equivalents of hydrogen chloride. Electrospray MS$^m$/z 573/575 [M+H]$^+$.

EXAMPLE 37
3-Phenylpropyl 4-(3,4-dichlorophenyl)-6-[(2-(N,N-diethylamino)ethylthio)methyl]-2-methylthio-1,4-dihydropyrimidine-5-carboxylate A mixture of 3-phenylpropyl 4-(2-(N,N-diethylaminoethylthio)methyl)acetoacetate (5.71 g, 16.24 mmol), 3,4-dichlorobenzaldehyde (3.13 g, 17.86 mmol), 2-methyl-2-thiopseudourea sulfate (2.49 g, 8.93 mmol) and sodium acetate (0.733 g, 8.93 mmol) was stirred in N,N-dimethylformamide (25 mL) for 3 days at room temperature, then heated to 60° C. for 3 days. The DMF was removed in vacuo and ethyl acetate was added to the residue. The precipitate was removed by filtration and the filtrate was washed with water, sodium hydrogen carbonate solution and brine, dried and evaporated to yield an oil. This oil was further purified by flash chromatography to give the title compound (0.026 g) as an oil.

Electrospray MS$^m$/z 580/582 [M+H]$^+$.

EXAMPLE 38
3-Phenylpropyl 4-(3,4-dichlorophenyl)-6-[(2-(N,N-diethylamino)ethoxy)methyl]-2-methylthio-1,4-dihydropyrimidine-5-carboxylate A mixture of 3-phenylpropyl 4-(2-(N,N-diethylamino)ethoxy)acetoacetate (2.0 g, 5.96 mmol), 3,4-dichlorobenzaldehyde (1.15 g, 6.56 mmol), 2-methyl-2-thiopseudourea sulfate (0.913 g, 3.28 mmol) and sodium acetate (0.27 g, 3.28 mmol) was stirred in N,N-dimethylformamide (10 mL) for 24 hours at room temperature, then heated to 60° C. for 5 days. The DMF was removed in vacuo and ethyl acetate was added to the residue. The precipitate was removed by filtration and the filtrate was washed with water, sodium hydrogen carbonate solution and brine, dried and evaporated to yield an oil. This oil was further purified by flash chromatography and RP-HPLC to give the title compound (114 mg) as an oil. The oil can be converted into a mono or dihydrochloride salt, by dissolution in ether and addition of one or two equivalents of hydrogen chloride. Electrospray MS$^m$/z 564/566 [M+H]$^+$.

Following the general procedure for Example 38, but using the appropriate acetoacetate derivative, the compounds of Examples 39 to 41 were synthesised:

EXAMPLE 39
3-Phenylpropyl 4-(3,4-dichlorophenyl)-6-[(2-(N,N-dimethylamino)ethoxy)methyl]-2-methylthio-1,4-dihydropyrimidine-5-carboxylate Electrospray MS$^m$/z 536/538 [M+H]$^+$.

EXAMPLE 40
3-Phenylpropyl 4-(3,4-dichlorophenyl)-2-methylthio-6-[(2-(4-morpholinyl)ethoxy)methyl]-1,4-dihydropyrimidine-5-carboxylate Electrospray MS$^m$/z 578/580 [M+H]$^+$.

EXAMPLE 41
3-Phenylpropyl 4-(3,4-dichlorophenyl)-6-[(2-(N,N-diethylamino)ethylamino)methyl]-2-methylthio-1,4-dihydropyrimidine-5-carboxylate Electrospray MS$^m$/z 529 [M+H]$^+$.

EXAMPLE 42
3-Phenylpropyl 6-(2-aminoethoxymethyl)-4-(3,4-dichlorophenyl)-2-methylthio-1,4-dihydropyrimidine-5-carboxylate A mixture of 3-phenylpropyl 4-(2-(2-(1,3-dihydro-1,3-dioxo-2H-isoindolyl)ethoxy)acetoacetate (2.25 g, 5.50 mmol), 3,4-dichlorobenzaldehyde (1.16 g, 6.60 mmol), 2-methyl-2-thiopseudourea sulfate (0.919 g, 3.30 mmol) and sodium acetate (0.27 g, 3.30 mmol) was stirred in N,N-dimethylformamide (10 mL) for 4 days at room temperature, then heated to 60° C. for 5 days. The DMF was removed in vacuo and ethyl acetate was added to the residue. The precipitate was removed by filtration and the filtrate was washed with water, sodium hydrogen carbonate solution and brine, dried and evaporated to yield an oil. This oil was further purified by flash chromatography to give 3-phenylpropyl 4-(3,4-dichlorophenyl)-6[(2-(1,3-dihydro-1,3-dioxo-2H-isoindol-2-yl) ethoxy)methyl]-2-thiomethyl-1,4-dihydropyrimidine-5-carboxylate (1.31 g) as an oil which then crystallized. Electrospray MS$^m$/z 638/640 [M+H]$^+$). This compound (800 mg, 1.2 mmol) was dissolved in methanol (2 mL) and chloroform (2 mL). Hydrazine hydrate (80 μL) was added and the mixture was stirred at room temperature for 72 h. The mixture was evaporated, the residue was dissolved in ethyl acetate and washed with sodium bicarbonate solution and then water, dried and evaporated. The title compound (126 mg) was isolated by preparative reverse phase HPLC as an oil. Electrospray MS$^m$/z 508/510 [M+H]$^+$.

EXAMPLE 43
Resolution of 3-phenylpropyl 4-(3,4-dichlorophenyl)-2-methylthio-6-[(2-(1-piperidinyl)ethoxy)methyl]-1,4-dihydropyrimidine-5-carboxylate Racemic 3-phenylpropyl 4-(3,4-dichlorophenyl)-2-methylthio-6-[(2-(1-piperidinyl)ethoxy)methyl]-1,4-dihydropyrimidine-5-carboxylate (Example 1, 1.30 g, 2.25 mmol) in warm ethyl acetate was added to D-DOBT (0.727 g, 2.03 mmol) in warm ethyl acetate. The mixture was allowed to stand for 5 days and then the precipitate was collected by filtration. This solid was partitioned between saturated sodium bicarbonate solution and ethyl acetate. The organic layers were combined, dried and evaporated to give the free base (0.340 g, 0.59 mmol). An ethanolic solution of hydrogen chloride (2.0 equivalents) was added to an ether solution of the free base and the resultant solid was collected by filtration to yield 3-phenylpropyl (+)-4-(3,4-dichlorophenyl)-2-methylthio-6-[(2-(1-piperidinyl)ethoxy)methyl]-1,4-dihydropyrimidine-5-carboxylate dihydrochloride salt (208 mg). Chiral HPLC in 17.5% CH$_3$CN—50 mM potassium dihydrogen phosphate buffer at pH 4.373 showed this material to be 98.6% one enantiomer. Optical rotation, $[α]_D$+59.8° (c=0.48, EtOH). Electrospray MS$^m$/z 576/578 [M+H]$^+$.

3-Phenylpropyl (-)-4-(3,4-dichlorophenyl)-2-methylthio-6-[(2-(1-piperidinyl)ethoxy)methyl]-1,4-dihydropyrimidine-5-carboxylate dihydrochloride salt was obtained by the same procedure but using L-DOBT. Chiral HPLC in 17.5% CH$_3$CN—50 mM potassium dihydrogen phosphate buffer at pH 4.373 showed this material to be 99.8% one enantiomer. Optical rotation, $[α]_D$-64.4° (c=0.39, MeOH). Electrospray MS$^m$/z 576/578 [M+H]$^+$.

EXAMPLE 44
3-Phenylpropyl 4-(3,4-dichlorophenyl)-2-methylthio-6-[(2-(1-N-methylpiperidinium)ethoxy)methyl]-1,4-dihydropyrimidine-5-carboxylate chloride The compound of Example 1 was treated with methyl iodide (2 equivalents). The resulting piperidinium quaternary iodide salt was isolated by RP-HPLC using a water/acetonitrile gradient containing trifluoroacetic acid as a modifier, and was converted into the corresponding chloride by repeated exposure to hydrogen chloride in ether. Electrospray MS$^m$/z 590/592.

We claim:

1. A compound of formula (I)

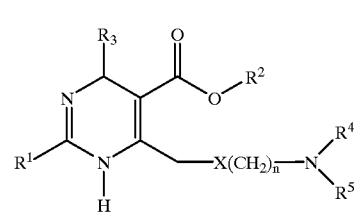

(I)

including its 3,4-dihydropyrimidine tautomer form wherein:

$R^1$ represents $SR^6$, $NR^6R^7$ or $OR^6$;

$R^2$ represents alkyl C1 or 6 or unsaturated alkyl C2 to 6, either optionally including O or S, and which is substituted by a phenyl or a monocyclic heteroaryl ring, which aromatic ring is optionally substituted by one or more substituents independently selected from halogen, alkyl C1 to 6 or alkoxy C1 to 6;

$R^3$ represents a monocyclic or bicyclic aromatic ring optionally incorporating one heteroatom selected from N, O or S, optionally substituted by one or more substituents independently selected from halogen, alkyl C1 to 6, alkoxy C1 to 6, cyano, trifluoromethyl, amino, hydroxy, nitro or carbomethoxy;

$R^4$ and $R^5$ independently represent hydrogen, alkyl C1 to 6, or benzyl;

or the group $NR^4R^5$ together represents piperidinyl, morpholinyl, 1,2,3,6-tetrahydropyridinyl, tetrahydro-4H-1,4-thiazinyl, pyrrolidinyl, N-methylpiperidinium, piperazinyl or piperazinyl further substituted at N-4 by alkyl C1 to 6;

$R^6$ and $R^7$ independently represent alkyl C1 to 6 or cycloalkyl C3 to 6, or benzyl, optionally substituted on the phenyl ring by alkyl C1 to 6, alkoxy C1 to 6 or halogen;

X represents O, S or $NR^8$;

$R^8$ represents hydrogen or alkyl C1 to 6;

and n represents an integer 2 to 4;

and optical isomers and racemates thereof and pharmaceutically acceptable salts thereof.

2. A compound of formula (I), according to claim 1, wherein $R^1$ represents $SR^6$ and $R^6$ represents alkyl C 1 to 6.

3. A compound of formula (I), according to claim 1, wherein $R^2$ represents 3-phenylpropyl or 3-(1-phenoxy)propyl, optionally substituted on the phenyl ring by halogen.

4. A compound of formula (I), according to claim 1, wherein $R^3$ represents a 4-substituted phenyl, optionally further substituted in the 2- or 3-position, or 2-quinolyl.

5. A compound of formula (I), according to claim 1, wherein $R^4$ and $R^5$ independently represent alkyl C 1 to 6, or the group $NR^4R^5$ together represents piperidinyl, pyrrolidinyl or piperazinyl further substituted at N-4 by alkyl C 1 to 6.

6. A compound of formula (I), according to claim 1, wherein X is O and n is 2.

7. A compound of formula (I), according to claim 1, wherein $R^1$ represents SMe; $R^2$ represents 3-phenylpropyl; $R^3$ represents a 4-substituted phenyl, optionally further substituted in the 3-position, or 2-quinolyl; $R^4$ and $R^5$ are both methyl or ethyl, or $NR^4R^5$ together represents piperidinyl or 4-methylpiperazinyl; X is O; and n is 2.

8. A compound of formula (I) which is:

3-phenylpropyl 4-(3,4-dichlorophenyl)-2-methoxy-6-[(2-(1-piperidinyl)ethoxy)methyl]-1,4-dihydropyrimidine-5-carboxylate, 3-phenylpropyl 4-(3,4-dichlorophenyl)-2-ethylthio-6-[(2-(1-piperidinyl)ethoxy)methyl]-1,4-dihydropyrimidine-5-carboxylate, 3-phenylpropyl 2-methylthio-4-(2-naphthyl)-6-[(2-(1-piperidinyl)ethoxy)methyl]-1,4-dihydropyrimidine-5-carboxylate, 3-phenylpropyl 2-methylthio-6-[(2-(1-piperidinyl)ethoxy)methyl]-4-(2-quinolyl)-1,4-dihydropyrimidine-5-carboxylate, 3-phenylpropyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3,5-dichlorophenyl)-2-methylthio-6-[(2-(1-piperidinyl)ethoxy)methyl]-1,4-dihydropyrimidine-5-carboxylate, 3-phenylpropyl 2-methylthio-4-(4-nitrophenyl)-6-[(2-(1-piperidinyl)ethoxy)methyl]-1,4-dihydropyrimidine-5-carboxylate, 2-(4-chlorophenoxy)ethyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(4-chlorophenyl)-2-methylthio-6-[(2-(1-piperidinyl)ethoxy)methyl]-1,4-dihydropyrimidine-5-carboxylate, 3-phenylpropyl 4-(3,5-bis(trifluoromethyl)phenyl)-2-methylthio-6-[(2-(1-piperidinyl)ethoxy)methyl]-1,4-dihydropyrimidine-5-carboxylate, 3-phenylpropyl 4-(4-methylphenyl)-2-methylthio-6-[(2-(1-piperidinyl)thoxy)methyl]-1,4-dihydropyrimidine-5-carboxylate, 3-phenylpropyl 4-(4-cyanophenyl)-2-methylthio-6-[(2-(1-piperidinyl)ethoxy)methyl]-1,4-dihydropyrimidine-5-carboxylate, 3-phenylpropyl (+)-4-(3,4-dichlorophenyl)-2-methylthio-6-[(2-(1-piperidinyl)ethoxy)methyl]-1,4-dihydropyrimidine-5-carboxylate, 3-phenylpropyl 4-(4-methyl-3-nitrophenyl)-2-methylthio-6-[(2-(1-piperidinyl)ethoxy)methyl]-1,4-dihydropyrimidine-5-carboxylate, 3-phenylpropyl 4-(4-chloro-3-nitrophenyl)-2-methylthio-6-[(2-(1-piperidinyl)ethoxy)methyl]-1,4-dihydropyrimidine-5-carboxylate, 3-phenylpropyl 4-(4-ethylphenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6-[(2-(N,N-diethylamino)ethylthio)methyl]-2-methylthio-1,4-dihydropyrimidine-5-carboxylate, 3-phenylpropyl 4-(4-iodophenyl)-2-methylthio-6-[(2-(1-piperidinyl)ethoxy)methyl]-1,4-dihydropyrimidine-5-carboxylate, 3-phenylpropyl 4-(4-bromophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6-[(2-(N,N-diethylamino)ethoxy)methyl]-2-methylthio-1,4-dihydropyrimidine-5-carboxylate, 3-phenoxypropyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(4-methoxycarbonylphenyl)-2-methylthio-6-[(2-(1-piperidinyl)ethoxy)methyl]-1,4-dihydropyrimidine-5-carboxylate, 3-phenylpropyl 4-(4-methoxyphenyl)-2-methylthio-6-[(2-(1-piperidinyl)ethoxy)methyl]-1,4-dihydropyrimidine-5-carboxylate, 3-phenylpropyl 2-methylthio-6-[(2-(1-piperidinyl)ethoxy)methyl]-4-(2-thienyl)-1,4-dihydropyrimidine-5-carboxylate, 3-phenylpropyl 2-methylthio-4-phenyl-6-[(2-(1-piperidinyl)ethoxy)methyl]-1,4-dihydropyrimidine-5-carboxylate, 3-phenylpropyl 4-(3,4-dichlorophenyl)-2-dimethylamino-6-[(2-(1-piperidinyl)ethoxy)methyl]-1,4-dihydropyrimidine-5-carboxylate, 2-(3-methylphenoxy)ethyl 4-(3,4-dichlorophenyl)-2-methylthio-6-[(2-(1-piperidinyl)ethoxy)methyl]-1,4-dihydropyrimidine-5-carboxylate, 2-phenoxyethyl 4-(3,4-dichlorophenyl)-2-methylthio-6-[(2-(1-piperidinyl)ethoxy)methyl]-1,4-dihydropyrimidine-5-carboxylate, 3-(3,4-dimethoxyphenyl)propyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3-chlorophenyl)-2-methylthio-6-[(2-(1-piperidinyl)ethoxy)methyl]-1,4-dihydropyrimidine-5-carboxylate, 2-phenethyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-2-(4-methoxyphenyl)methylthio-6-[(2-(1-piperidinyl)ethoxy)methyl]-1,4-dihydropyrimidine-5-carboxylate, 3-phenylpropyl 4-(4-isopropylphenyl)-2-methylthio-6-[(2-(1-piperidinyl)ethoxy)methyl]-1,4-dihydropyrimidine-5-carboxylate, 3-phenylpropyl 4-(3,4-dichlorophenyl)-2-methylthio-6-[(4-(1-piperidinyl)butyloxy)methyl]-1,4-dihydropyrimidine-5-carboxylate, 3-phenylpropyl 2-methylthio-6-[(2-(1-piperidinyl)ethoxy)methyl]-4-(4-trifluoromethylphenyl)-1,4-dihydropyrimidine-5-carboxylate, 3-phenylpropyl 2-methylthio-4-(3-nitrophenyl)-6-[(2-(1-piperidinyl)ethoxy)methyl]-1,4-dihydropyrimidine-5-carboxylate, 3-(4-methoxyphenyl)propyl 4-(3,4-dichlorophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6-[(2-(N,N-dimethylamino)ethoxy)methyl]-2-methylthio-1,4-dihydropyrimidine-5-carboxylate, 3-phenylpropyl 6-(2-aminoethoxymethyl)-4-(3,4-dichlorophenyl)-2-methylthio-1,4-dihydropyrimidine-5-carboxylate, 3-phenylpropyl 4-(3,4-dichlorophenyl)-2-methylthio-6-[(2-(4-morpholinyl)ethoxy)methyl]-1,4-dihydropyrimidine-5-carboxylate, 3-phenylpropyl (−)-4-(3,4-dichlorophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-6-[(2-(N,N-diethylamino)ethylamino)methyl]-2-methylthio-1,4-dihydropyrimidine-5-carboxylate, 3-phenylpropyl 4-(3-hydroxy-4-nitrophenyl)-2-methylthio-6-[(2-(1-piperidinyl)ethoxy)methyl]-1,4-dihydropyrimidine-5-carboxylate, 3-phenylpropyl 4-(4-hydroxy-3-nitrophenyl)-2-methylthio-6-[(2-(1-piperidinyl)ethoxy)methyl]-1,4-dihydropyrimidine-5-carboxylate, 3-phenylpropyl 4-(3,4-dichlorophenyl)-2-methylthio-6-[(2-(1-N-methylpiperidinium)ethoxy)methyl]-1,4-dihydropyrimidine-5-carboxylate chloride, or an optical isomer or racemate or tautomer of any one thereof or a pharmaceutically acceptable salt of any one thereof.

9. A compound of formula (I), as defined in claim 1, or an optical isomer or racemate or tautomer thereof or a pharmaceutically acceptable salt thereof, for use as a medicament.

10. A pharmaceutical formulation comprising a compound of formula (I), as defined in claim 1, or an optical isomer or racemate or tautomer thereof or a pharmaceutically acceptable salt thereof, optionally in admixture with a pharmaceutically acceptable diluent or carrier.

11. A method of treating, or reducing the risk of, human diseases or conditions in which inhibition of N-type neuronal calcium channel activity is beneficial which comprises administering to a person suffering from or susceptible to such a disease or condition, a therapeutically effective amount of a compound of formula (I), as defined in claim 1, or an optical isomer or racemate or tautomer thereof or a pharmaceutically acceptable salt thereof.

12. A method of treating, or reducing the risk of, cerebrovascular ischaemia or stroke or head trauma or cardiac arrest or neurodegenerative disorders or pain or psychotic disorders or affective disorders which comprises administering to a person suffering from or susceptible to such a disease or condition, a therapeutically effective amount of a compound of formula (I), as defined in claim 1, or an optical isomer or racemate or tautomer thereof or a pharmaceutically acceptable salt thereof.

13. A method of treatment according to claim 12, wherein the condition to be treated is selected from the group consisting of cerebrovascular ischaemia, stroke, head trauma, Alzheimer's disease, schizophrenia and pain.

14. A method of treatment according to claim 13, wherein the condition to be treated is cerebrovascular ischaemia.

15. A method of treatment according to claim 13, wherein the condition to be treated is stroke.

16. A method of treatment according to claim 13, wherein the condition to be treated is head trauma.

17. A method of treatment according to claim 13, wherein the condition to be treated is pain.

18. A method of treatment according to claim 13, wherein the condition to be treated is Alzheimer's disease.

19. A method of treatment according to claim 13, wherein the condition to be treated is schizophrenia.

20. A process for the preparation of a compound of formula (I), as defined in claim 1, and optical isomers and racemates and tautomers thereof and pharmaceutically acceptable salts thereof, which comprises:

(a) preparing a compound of formula (I) by reacting a corresponding compound of formula (II)

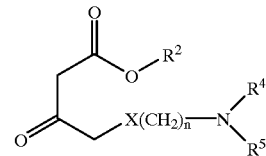

(II)

wherein $R^2$, $R^4$, $R^5$, X and n are as defined in claim 1 with a compound of formula (III) or an acid addition salt thereof

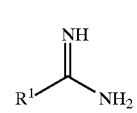

(III)

wherein $R^1$ is as defined in claim 1 and with a compound of formula (IV)

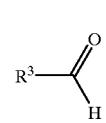

(IV)

wherein $R^3$ is as defined in claim 1; or (b) preparing a compound of formula (I) by reacting a corresponding compound of formula (V)

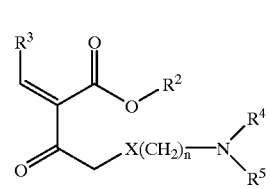

(V)

wherein $R^2$, $R^3$, $R^4$, $R^5$, X and n are as defined in claim 1
with a compound of formula (III) or an acid addition salt thereof

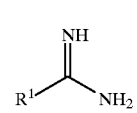

(III)

wherein $R^1$ is as defined in claim 1; or (c) preparing a compound of formula (I) by reacting a corresponding compound of formula (VI)

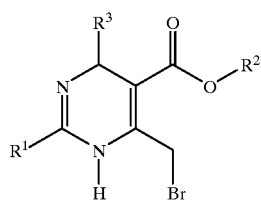 (VI)
wherein R¹, R² and R³ are as defined in claim 1 with a compound of formula (VII)
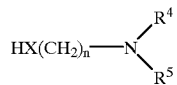 (VII)
wherein $R^4$, $R^5$, X and n are as defined in claim 1; and where desired or necessary converting the resultant compound of formula (I), or another salt thereof, to a pharmaceutically acceptable salt thereof, or vice versa.
* * * * *